(12) United States Patent
Farberov

(10) Patent No.: US 6,942,343 B2
(45) Date of Patent: Sep. 13, 2005

(54) OPTICAL DEVICE FOR INTRAOCULAR OBSERVATION

(76) Inventor: Arkadiy Farberov, 42257 Troyer Ave., Fremont, CA (US) 94539

( * ) Notice: Subject to any disclaimer, the term of this patent is extended or adjusted under 35 U.S.C. 154(b) by 278 days.

(21) Appl. No.: 10/409,428

(22) Filed: Apr. 7, 2003

(65) Prior Publication Data

US 2004/0196431 A1 Oct. 7, 2004

(51) Int. Cl.⁷ ................................................ A61B 3/00
(52) U.S. Cl. ............................... 351/219; 606/4; 606/5; 606/10; 351/205
(58) Field of Search ............................ 351/200, 205, 351/216, 219, 220, 221, 246, 160 H, 160 R; 604/289; 606/4–6, 10; 607/53–54

(56) References Cited

U.S. PATENT DOCUMENTS

| 3,820,879 A | | 6/1974 | Frisen |
| 4,065,208 A | * | 12/1977 | Currey ........................ 351/219 |
| 4,134,647 A | | 1/1979 | Ramos-Caldera |
| 4,439,026 A | | 3/1984 | Wilms |
| 4,506,962 A | * | 3/1985 | Roussel .................. 351/160 R |
| 4,568,157 A | | 2/1986 | Kurwa |
| 4,598,984 A | * | 7/1986 | Rol ............................ 351/219 |
| 4,664,490 A | | 5/1987 | Rol |
| 5,031,622 A | * | 7/1991 | LaHaye ....................... 600/398 |
| 5,252,998 A | | 10/1993 | Reis et al. |
| 5,359,372 A | | 10/1994 | Kida |
| 5,479,222 A | * | 12/1995 | Volk ........................... 351/219 |
| 5,490,849 A | * | 2/1996 | Smith ............................. 606/5 |
| 5,501,217 A | | 3/1996 | Ishiguro et al. |
| 5,537,164 A | | 7/1996 | Smith |
| 5,548,352 A | * | 8/1996 | Dewey .................... 351/160 H |
| 5,841,510 A | * | 11/1998 | Roggy ......................... 351/218 |
| 6,183,085 B1 | * | 2/2001 | Roggy et al. ................ 351/200 |

OTHER PUBLICATIONS

"Goniscopy and Peripheral Retina" by Dr. Riley. School of optometry, Course of Lectures, Indiana University, 2003.

* cited by examiner

Primary Examiner—Brian L. Casler
Assistant Examiner—John R. Sanders

(57) ABSTRACT

The gonioscope of the invention comprises a hollow tapered body with mirror surfaces formed on the inner side of the gonioscope or on the inserts placed into the recesses on the inner surface of the gonioscope. Several reflecting surfaces arranged at the same or different angles can be used. The device can be made disposable and molded with reflecting surface coatings applied onto the inner flats. According to one of the embodiments, the gonioscope can be used in combination with a meniscus lens that can applied onto the eye cornea and used as a support for sliding the front end of the gonioscope over the lens surface for orientation thereof at different angles to the optical axis of the eye.

4 Claims, 10 Drawing Sheets

OPTICAL DEVICE FOR INTRAOCULAR OBSERVATION

FIELD OF THE INVENTION

The present invention relates to optical devices, in particular to optical devices for intraocular observation, diagnosis, treatment, or the like, especially on angle portions, in an eyeball.

BACKGROUND OF THE INVENTION

For better understanding the principle of the present invention and for understanding the areas of application of the invented device, it would be advantageous to briefly familiarize yourself with anatomy of the eye. FIG. 1 is a cross-sectional view of a human eye. The definitions of the terms some of which is used in the description of the present patent application are given below.

The anterior chamber is the area bounded in front by the cornea and in back by the lens, and filled with aqueous.

The choroid, which carries blood vessels, is the inner coat between the sclera and the retina.

The ciliary body is an unseen part of the iris, and these together with the ora serrata form the uveal tract.

The conjunctiva is a clear membrane covering the white of the eye (sclera).

The cornea is a clear, transparent portion of the outer coat of the eyeball through which light passes to the lens.

Fundus is an inner wall of the eye.

The iris gives our eyes color and it functions like the aperture on a camera, enlarging in dim light and contracting in bright light. The aperture itself is known as the pupil.

The macula is a small area in the retina that provides our most central, acute vision.

The optic nerve conducts visual impulses to the brain from the retina.

The ora serrata and the ciliary body form the uveal tract, an unseen part of the iris.

The posterior chamber is the area behind the iris, but in front of the lens, that is filled with aqueous.

The pupil is the opening, or aperture, of the iris.

Retina is the innermost coat of the back of the eye, formed of light-sensitive nerve endings that carry the visual impulse to the optic nerve.

The retina may be compared to the film of a camera.

The sclera is the white of the eye.

The vitreous is a transparent, colorless mass of soft, gelatinous material filling the eyeball behind the lens.

The techniques used for viewing the inner parts of the eye, such as retina and anterior chamber angle of the eye for evaluation, management, and classification of normal and abnormal structures is known as gonioscopy, and devices used for gonioscopy are known as gonioscopes. Observation of the anterior chamber and especially its angle areas, which are difficult or impossible to see with the use of some conventional optical means, is very important for diagnosis of eye diseases. For example, the classification of glaucoma relies heavily upon knowledge of the anterior segment anatomy, particularly that of the anterior chamber angle.

The anterior chamber of a human eye is commonly evaluated during slit lamp biomicroscopy, but the chamber angle is hidden from ordinary view because of total internal reflection of light rays emanating from the angle structures. In other words, without gonioscopy, the additional diagnostic clues of disease are forever hidden from ordinary view. It requires additional effort, skill and patient co-operation to view the normally concealed chamber angle by either indirect (angle structures viewed through a mirror) or direct (angle structures viewed directly) gonioscopic techniques. In other words, without gonioscopy, it is impossible to classify the glaucoma properly.

Heretofore, many gonioscopic devices have been known. The basic gonioscopic instrument used in the art is known as a Goldman "unversal" lens and mirrors or Roussel lens assembly. This gonioscope comprises an optical body with flat tapered sides having an entrance face which is flat or spherical, a spherical exit face which is applied to the cornea of the eye, a reflecting face and a compensating element, for example a plano-cylindrical lens. The Goldman gonioscope is a universal three-reflection lens assembly for biomicroscopic investigation and laser coagulation of the eye bottom and the front camera angle of the eye. With the help of lenses by Goldman in combination with a binocular microscope of a slit lamp a high quality image, a step-by-step observation of the eye bottom up to a tooth-like line, gonioscopy, detection of minute variation of eye structures under observation and spatial-depth localization of pathologic structures are provided.

Many other modifications of the Goldman gonioscope are known. Some of them are described below.

For example, U.S. Pat. No. 3,820,879 issued in 1974 to L. Frisen describes a contact glass device for biomicroscopic examination of the human eye comprising a lens body with a concave surface adapted for application upon the cornea of the eye to be examined with the optical axis of the lens coinciding with the optical axis of the eye and two light reflecting mirrors disposed at the side of the lens body opposite to the aforementioned concave surface so that the reflecting mirrors face each other on opposite sides of the optical axis of the lens. Furthermore, the mirrors are inclined at such angles relative to the optical axis of the lens body and to each other that it is possible to view the interior of an eye, on which the lens body is applied with its concave surface, in a non-reversible manner along a line of view which is reflected in the two mirrors and passes through the lens body. In one embodiment of the invention, one of the mirrors is pivoted relative to the lens body and allows observation of the anterior chamber from the central portion of the fundus of the eye radially outwardly to the boundary region of the fundus. Although the gonioscope of this type is efficient in its action, it cannot be easily sterilized because it comprises a complicated optical assembly.

U.S. Pat. No. 4,439,026 issued in 1984 to K. Wilms discloses an optical device with two reflecting surfaces which contains a contact glass with two reflecting surfaces for observing the chamber angle of a human eye in proximity of the iris, with a reflecting surface arranged laterally of the eye to be examined and a central reflecting surface to be located in the area of the common optical axis of the eye and of the axis of the contact glass. The path of observation rays is guided from the eye of the observer to the central reflecting surface and from the latter by way of the lateral reflecting surface into the interior of the eye whereby the lateral reflecting surface is so arranged to the common axis that its plane intersects the eye to be examined outside of the corneal area thereof and extends toward the eye to be examined up to a point to the rear of the center tangent of the eye abutment surface of the contact glass. In general, from the optical point of view the structure of this gonioscope is the same as in the previous patent and differs from it only by the fact that all reflecting angles are fixed and that the device has a monolithic structure more convenient for cleaning and sterilization. Various angles of observation may be achieved only by using a set of gonioscopes with different angles of reflecting mirrors.

U.S. Pat. No. 4,134,647 issued in 1979 to Ramos-Caldera discloses a contact lens for examining the interior of the eye. The inner walls of the eye, i.e., the fundus, are examined in panorama with an optical lens comprising a truncate paraboloidal mirror and a corneal contact objective lens. While held in contact with the cornea, the fundus is observed by projecting a light beam into the eye through the lens and viewing the interior eye with a microscope, e.g., a standard slit lamp instrument. Although this gonioscope allows seeing some hard-to-reach areas of the eye fundus, it has only one paraboloidal mirror, whereby the scope of observation is limited as compared to a conventional three-mirror Goldmal gonioscope.

U.S. Pat. No. 4,568,157 issued in 1986 to B. Kurwa describes a gonioscope that includes a truncated generally pyramidal body having four reflective sides, a concave smaller end face and an angled larger upper end face. The angled upper end face permits the use of a standard operating microscope since light produced by the microscope is reflected off-axis from the surface to minimize glare. The smaller end face has a curvature of approximately 43 diopters in order to seal mate with the human eye. The reflective sides of the lens enable the angle of the anterior chamber to be viewed by gonioscopy. The ratio of the height of lens to the width of its base is advantageously less than 2 and most advantageously approximately 1. The gonioscope of this type has a geometry modified for use only in combination with a microscope.

The idea of using curvilinear mirrors is further developed in U.S. Pat. No. 4,664,490 issued to P. Rol in 1987, which describes a monolithic gonioscopic lens of a conical shape for observation or treatment by irradiation of the eye, in particular the anterior chamber, outside of the optical axis of the eye. The device comprises a lens Goldman or Roussel lens, which, as has been described above, has flat tapered sides with an entrance face which is flat or spherical, a spherical exit face which is applied to the cornea of the eye, a reflecting face and a compensating element, for example a plano-cylindrical lens. The compensating element is fixed on the reflecting face and its function is to create an astigmatism effect, which is the reverse of that of the eye, for an incident light beam, which enters by way of the entrance face. It is understood that manufacture of aforementioned curvilinear compensation mirrors is a very complicated and expensive procedure. Furthermore, since curvatures on the anterior chambers vary from eye to eye, the approach used in the aforementioned patent may have a limited effect or requires a set of lenses.

U.S. Pat. No. 5,252,998 issued in 1993 to W. Reis et al. describes an instrument for the examination and/or treatment of the eye having an examination device designed for the examination of the fundus of the eye and having a contact eyeglass, which is provided with a lens which can be placed on the eye, the eye-facing surface of the lens being adapted to the curve of the cornea. The lens, which is placed on the eye, has no spherical power at least in the region of the optical axis. The device of the invention comprises a set of reflecting surfaces which are arranged at predetermined fixed angles in order to have an access to various hard-to-see areas of the eye fundus inaccessible with Goldman or Roussell lenses of other designs, e.g., such as one disclosed in U.S. Pat. No. 4,439,026 and U.S. Pat. No. 3,820,879. However, the gonioscope of this type requires the use of several mirrors located not on the side surfaces but rather in the central part of the gonioscope. As a result, the aperture of this optical device is reduced, and the light power is lost.

U.S. Pat. No. 5,359,372 issued in 1994 to H. Kida, et al. discloses a gonioscope for intraocular observation capable of optically recognizing an inner portion of an eyeball by contacting the contact lens on a surface of a cornea of an eye to be inspected through a light ray transmitted through an inner portion of the contact lens. The devices comprises: an optical path dividing member provided on an optical path for leading a light ray incident on the inner portion of the contact lens to the eye to be inspected for dividing a portion of the light ray on said optical path; and an index (image of an index mark) provided at a position approximately optically conjugate with a portion to be observed of the eye to be inspected on a divided optical path divided by the optical path dividing member. The portion to be observed and said index can be optically recognized by at least partially superposing a first image of the index on a second image of the portion to be observed. This device is specifically pointed out at the use of an index image and has limitations with regard to the areas of observation.

U.S. Pat. No. 5,501,217 issued in 1996 to S. Ishiguro, et al. discloses a gonioscope for intraocular observation including a lens body having a contact face to be brought into contact with cornea of an eyeball of a subject, and a lens support having a contact portion to be settled on sclera of the eyeball of the subject, the lens body and the lens support being assembled on each other by means of a slide mechanism so as to be movable relative to each other in the axial direction of the gonioscope, wherein the gonioscope body is capable of pressing the cornea of the eyeball of the subject by movement thereof in the axial direction of device relative to the lens support settled on the sclera of the eyeball of the subject. The contact lens of the present invention is of good operability and adapted to effectively prevent slipping of itself on the cornea of an eyeball. Optically, the gonioscope of this type is the same as conventional ones, but is more convenient in practice as it consists of two relatively moveable parts one of which is used as a support on the eye.

U.S. Pat. No. 5,537,164 issued in 1996 to A. Smith describes a retroilluminating indirect gonioprism comprising an optical prism, an oblique reflector and light baffle to reduce the intensity of light reflected from the gonioprism anterior surface back toward an observer, and an opaque surface to substantially prevent retinal burns when using the gonioprism with a directed energy beam. Retroillumination of anterior chamber structures is provided by fiber optics incorporated into the gonioprism housing, which direct light from an external source into the peripheral portion of the eye anterior chamber. This retroillumination increases the accuracy of identification of structural landmarks (e.g., the scleral spur) which are important in argon laser trabeculoplasty. A directed energy beam, as from a high-energy laser, may be directed through the gonioprism while an eye structure on which the beam is focused is observed through the gonioprism. First-surface reflection of a portion of the directed energy beam passes obliquely toward a light baffle and is substantially absorbed, while the transmitted portion of the beam is slightly laterally displaced and strikes the gonioprism anterior surface. The portion of the beam reflected from the gonioprism anterior surface back toward the observer again undergoes partial reflection oblique to the visual axis and slight lateral displacement before reaching the observer. Thus, the amount of light reflected from the gonioprism anterior surface back toward an observer is reduced. Substantial optical correction for astigmatism of oblique incidence and for assuring substantial parallelism between the observer's line-of-sight to the gonioprism and the gonioprism optical axis is preferably provided through appropriate configuration of at least one substantially convex surface which comprises at least a portion of the optical prism anterior surface. The gonioscope described in the above patent makes it possible to perform a laser operation on the eye simultaneously with observation of the operation sight through the same gonioscope. The device is complicated, expensive, and the use thereof for simple observation and diagnostic is unjustifiable.

Thus, it can be concluded that all gonioscopes, which are known to the applicant and some of which have been described above, have common drawbacks in that they have complicated fragile and delicate structures and are expensive in production. In most cases the known gonioscopes are specialized for specific operations and therefore have limited application. The reflective optical surfaces are open and can be easily damaged. In addition, the exposed mirror surfaces may be damaged during sterilization. In view of their high cost, all of them are not disposable.

OBJECTS AND SUMMARY OF THE INVENTION

It is an object of the present invention to provide a gonioscope for observation of various areas inside an eye which is simple in construction, inexpensive to manufacture, versatile in application, can be produced with different angles of inclination of the flats on the inner surface of the gonioscope, allows observation of the most hard-to-see areas of the fundus, have internal location of mirrors for protection against damage in cleaning and sterilization, can be produced in a disposable form by molding, may be combined with meniscus lenses applied onto the eye cornea, and may has permanent or replaceable mirror inserts with the same or different angles of inclination of the reflecting surfaces with respect to the longitudinal axis of the gonioscope.

The gonioscope of the invention comprises a hollow tapered body with mirror surfaces formed on the inner side of the gonioscope or on the inner surfaces of the inserts which are placed into the recessed on the inner surface of the gonioscope. Several reflecting surfaces can be arranged at the same or different angles to the longitudinal axis of the gonioscope. In the second embodiment the gonioscope can be made disposable and molded with reflecting surface applied after molding onto the inner flats by evaporation in vacuum, or by other methods. In a third embodiment the gonioscope is used in combination with a meniscus lens, which is applied onto the eye cornea and is attached to or is separate from the gonioscope body and is used as a support for sliding the front end of the gonioscope over the lens surface for orientation thereof at different angles to the optical axis of the eye. In a fourth embodiment, the gonioscope is an assembly of the tapered body with the mirror inserts placed into the recesses on the inner surface of the hollow gonioscope.

DETAILED DESCRIPTION OF THE INVENTION

The invention will now be described in detail with reference to the drawings which illustrate various embodiments of the gonioscope of the invention.

Figure 1:
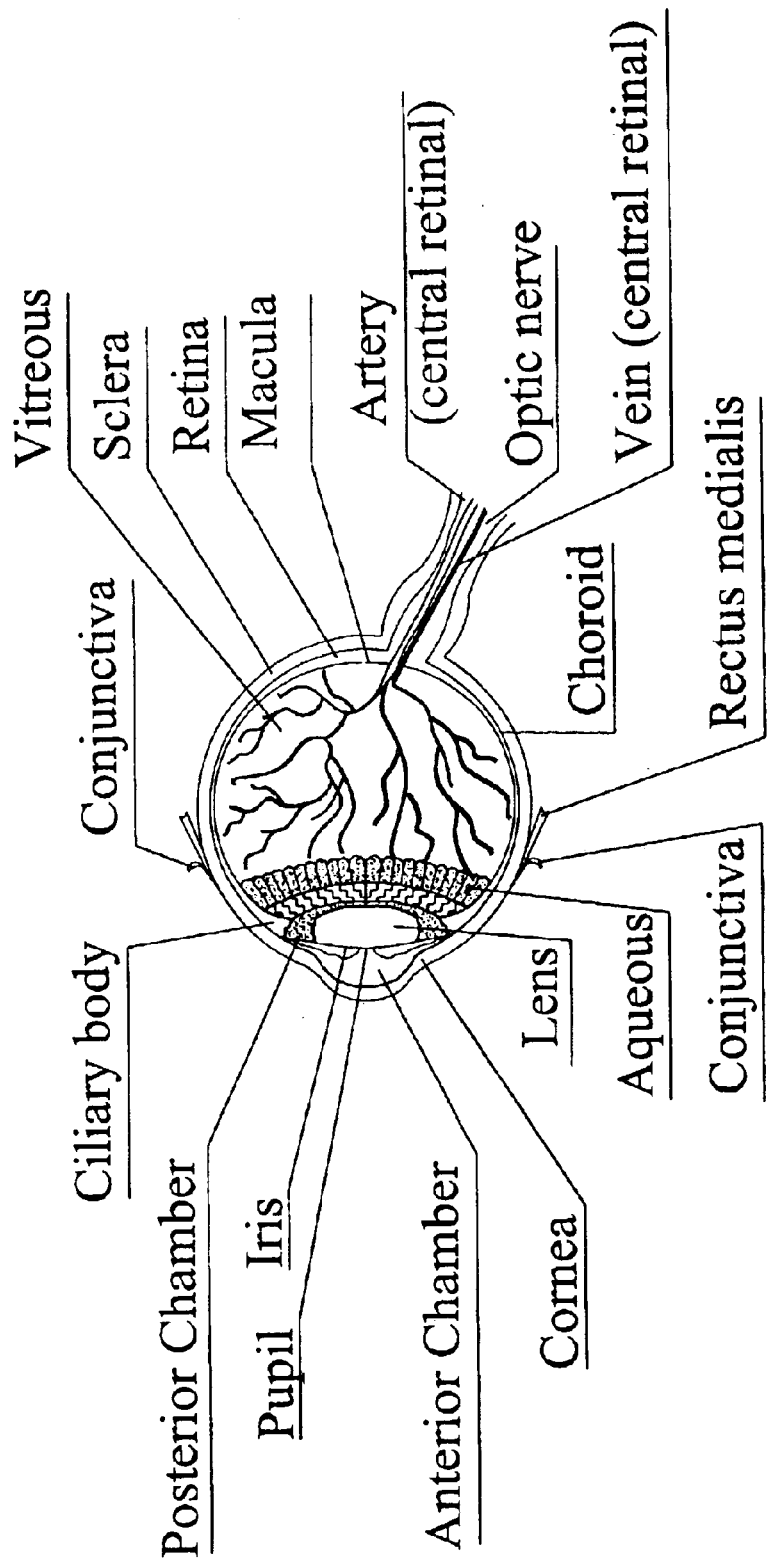
FIG. 1 is a cross-sectional view of a human eye.
Figure 2:
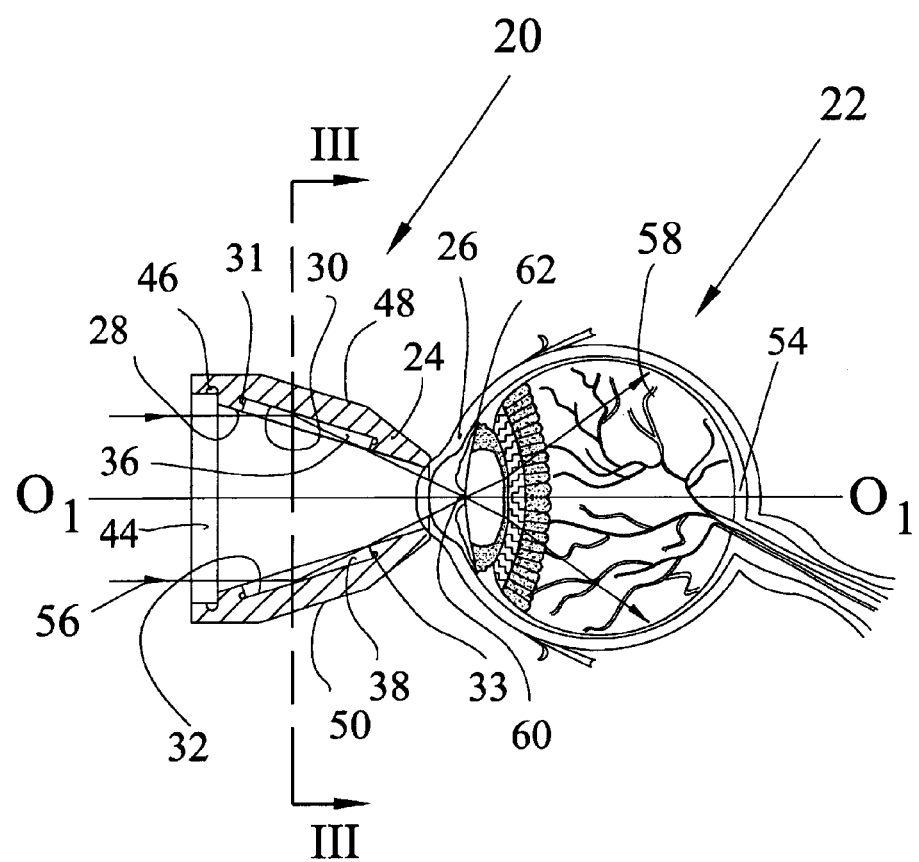
FIG. 2 is a longitudinal sectional view of a reusable gonioscope made in accordance with a first embodiment of the invention.

FIG. 2 is a longitudinal sectional view of a reusable gonioscope 20 made in accordance with a first embodiment of the invention. The gonioscope 20 is shown in a working position on a patient's eye 22 with a central optical axis $O_1$–$O_1$ of the gonioscope coinciding with the central axis of the eye. The gonioscope 20 has a hollow tapered body 24 molded from a biocompatible plastic which is allowed for contact with the cornea 26 of the eye. Examples of such plastics are the following: polycarbonate, acrylic, or the like.

Figure 3:
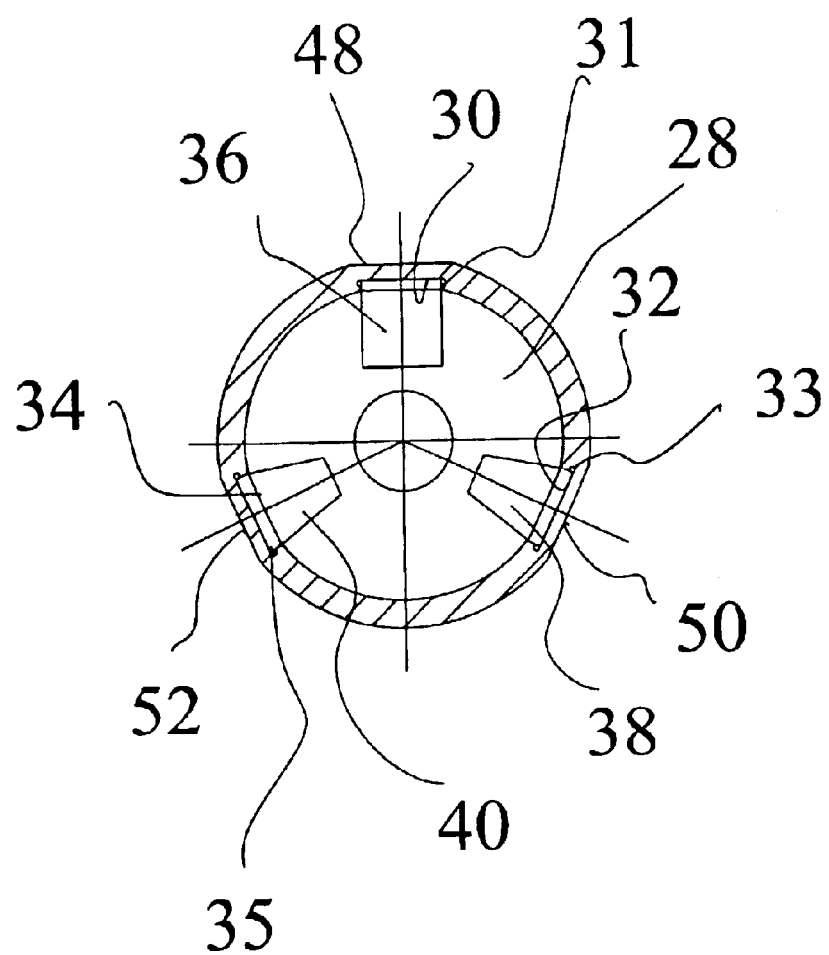
FIG. 3 is a cross-sectional view of the gonioscope along the line III—III of FIG. 2.

FIG. 3 is a cross-sectional view of the gonioscope 20 along the line III—III of FIG. 2. The inner surface 28 of the body 24 has at least one, but preferably a plurality of recesses 31, 33, 35. In FIG. 2 the diametrical arrangement of the recesses 31 and 33 is shown conventionally. It is understood that three recesses are shown as an example and that their number may be less or greater than three. The recesses 31, 33, 35 accommodate reflection mirror inserts 36, 38, 40, respectively, with the mirror surfaces 30, 32, and 34 formed, e.g., by mirror metal coatings formed on the inner sides of the mirror inserts so that the mirror surfaces are not exposed to the cavity of the hollow gonioscope body 24 (FIGS. 2 and 3) and thus protected from damage during cleaning. In order to diminish the effect of double refraction, the mirror inserts are made from thin transparent glass plates with mirror surfaces on the inner side of the insert, i.e., on the side facing away from cavity of the hollow gonioscope body 24.

Reference numeral 44 designates a protective glass cover installed in a recess 46 on the large-diameter side of the gonioscope body 24. The use of the glass cover 44 is optional. Another optional feature that can be used for convenience of grasping and holding is formation of flats 48, 50, and 52 (FIGS. 2 and 3) on the outer tapered surface of the body 24. The surfaces of the flats 48, 50, and 52 may be roughened for increase of the friction coefficient.

In operation, e.g., for examination or diagnosing conditions on the retina 54 of the eye 22, the gonioscope 20 is gently placed with its small-diameter end on the cornea 26 of the eye 22 after appropriate therapeutic procedures, such as anesthesia, application of a cushioning agent, etc., which are beyond the scope of the present invention. The inner surface of the selected mirror, e.g., the mirror 32 (FIG. 2) is illuminated by a light beam 56 from an external light source (not shown). The beam 56 is reflected from the mirror surface 38 (FIG. 3) and illuminates, e.g., the retina 54, in the area 58 remote from the optical axis $O_1$–$O_1$ of the eye 22.

Generally speaking, illumination of the areas to which the beam 56 is incident occurs in a certain solid angle which depends on the inlet aperture of the eye pupil 60. The light incident on the retina is scattered and illuminates the entire inner cavity of the eye.

Various inner potions of the eye retina 54, which are illuminated with the external light, in turn, emits secondary light which can be seen through the eye pupil 60 and mirrors 36, 38, and 40. Depending on the angle of observation and the selected mirror, the ophthalmologist can see various portions of the retina 54, including those remote from the optical axis of $O_1$–$O_1$ of the eye 22.

Figure 4:
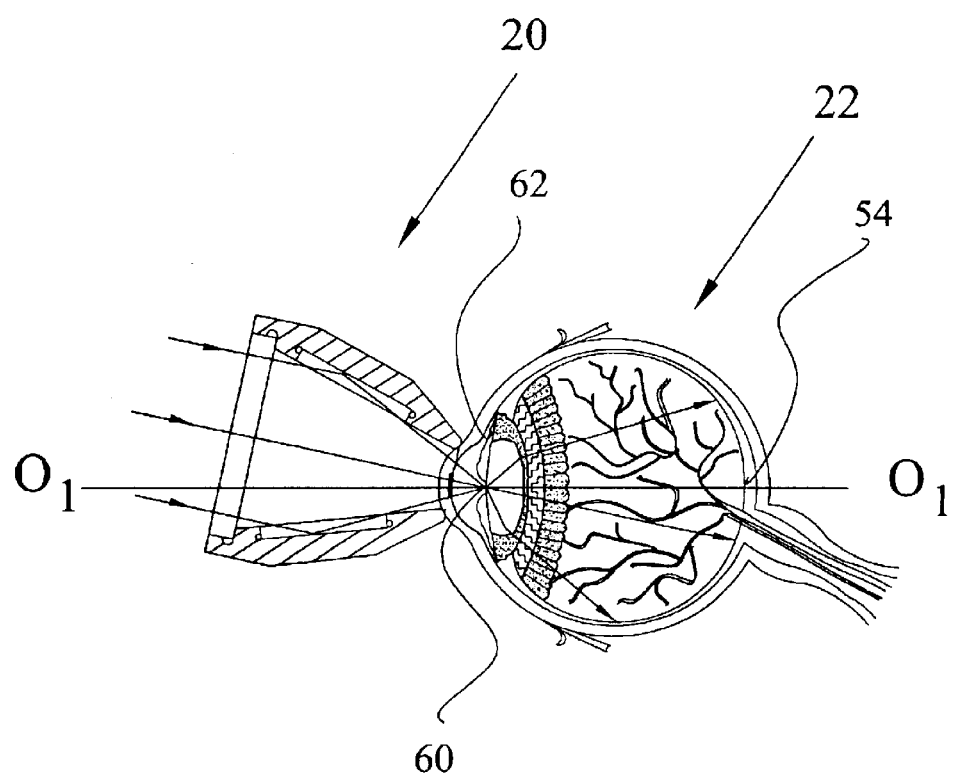
FIG. 4 is a view similar to FIG. 2 illustrating the gonioscope in another position on the eye cornea.

By manipulating the gonioscope 20 on the eye cornea 26, the ophthalmologist can see various peripheral areas inside the eye, e.g., the anterior chamber angle 62 (FIG. 4).

Figure 5:
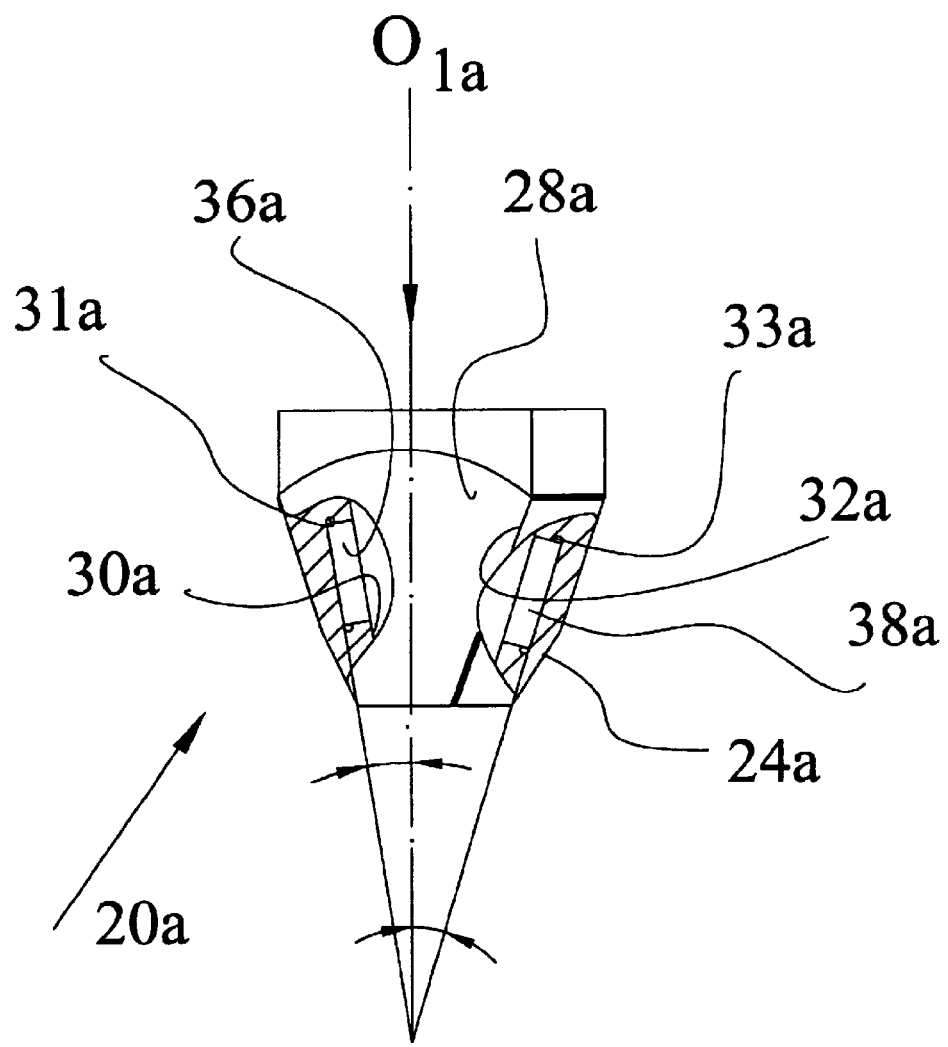
FIG. 5 is a side view of a gonioscope of a second embodiment with a part of the gonioscope body cut out to show the position of mirror inserts in recesses of flats inclined at different angles to the longitudinal axis of the gonioscope.
Figure 6A:
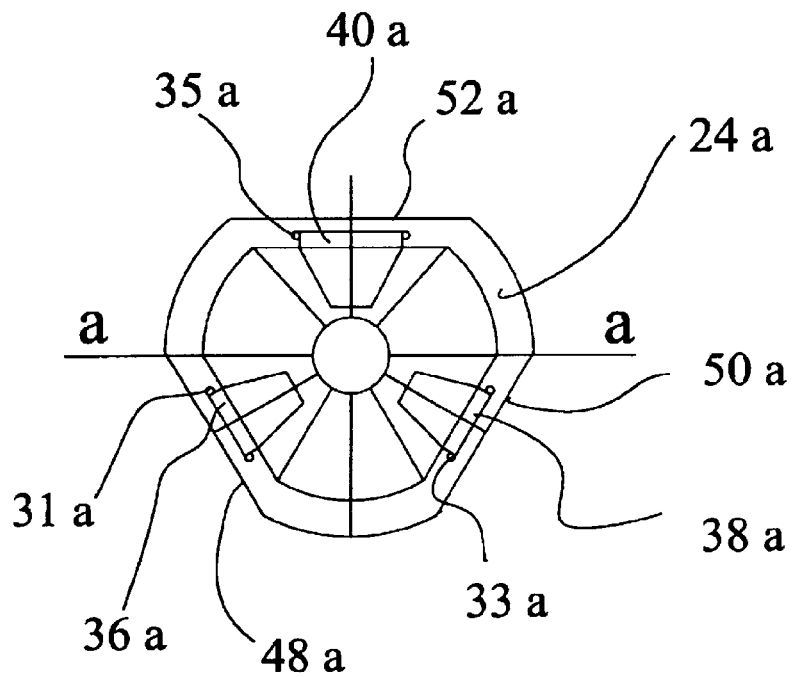
FIG. 6A is a view in the direction of arrow A of FIG. 5.
Figure 6B:
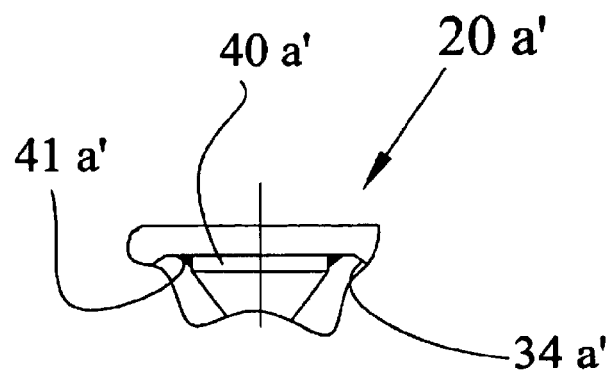
FIG. 6B is a fragmental view of one of the mirrors on the inner surface of the gonioscope.

FIG. 5 illustrates a second embodiment of the invention. FIG. 6A is a view in the direction of arrow A of FIG. 5. In this embodiment, those parts and elements of the gonioscope that are identical to those of the previous embodiment are designated by the same reference numbers with an addition of letter "a". A gonioscope 20a comprises a tapered body 24a with flats 30a and 32a formed on the inner surface 28a of the tapered body 24a. The flats 30a, 32a, and 34a (only 30a and 32a are seen on FIG. 5) may have shallow recesses 31a, 33a, and 35a (only 31a and 33a are sheen on FIG. 5) having the depth equal to the thickness of the glass plate mirrors 36a, 38a, and 40a inserted into the aforementioned recesses 31a, 33a, and 35a (only 36a, 38a are seen on FIG. 5), respectively. The glass plate mirrors can be fixed in the recesses by glue. If necessary, as shown in FIG. 6B which is a fragmental view of one mirror on the inner surface 28a' of the gonioscope 20a', the flats, such as the flat 34a', may be formed without recesses, and the mirrors, such as the mirror 40a', can be glued directly to the flats by means of glue 41a'.

If necessary, in the embodiment of FIG. 6A, the mirrors 36a, 36a, and 40a may be secured in the respective recesses 31a, 33a, and 35a by press fit instead of the adhesive connection.

As shown in FIG. 5, the flats 32a and 34a are cut with different taper angles. Thus, the flat 30a forms an angle α with the central longitudinal axis $O_{1a}$–$O_{1a}$ of the gonioscope 20a and the flat 32a forms an angle β with the central longitudinal axis $O_{1a}$–$O_{1a}$. The aforementioned longitudinal axis passes through the centers of the small-diameter side and the large-diameter side of the gonioscope. It is understood that the number of the flats may be different from three and that all of them may have the same or different angles at each flat. Although the flats 32a, 34a, and 36a are equally spaced from each other in the circumferential directions, the angular distances between them may be different.

Reference numerals 48a, 50a, and 52a designate external flats formed on the outer surface of the gonioscope body 24a for convenience of holding the device. If necessary, the surfaces of these flats can be roughened.

Figure 7:
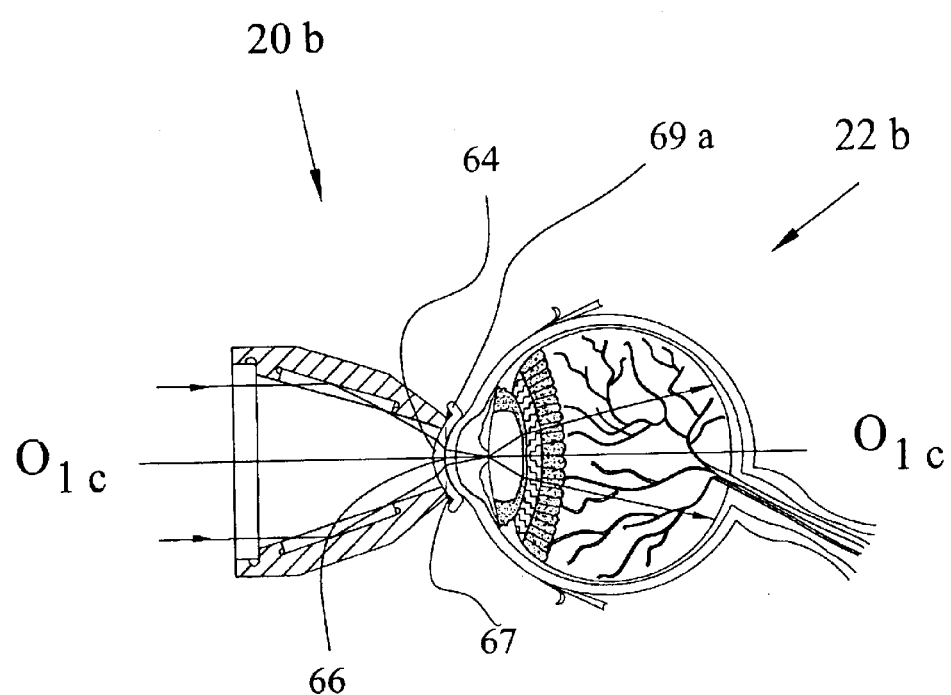
FIG. 7 is an embodiment in which the gonioscope of the invention is used in combination with meniscus lens applied onto the eye cornea.

An essential feature of the present invention is the use of the gonioscope of the invention in combination with a lens having a concave surface towards the patient and installed on the small-diameter end of the gonioscope. This can be a so-called contact Hruby lens, Goldman lens, or any other lens that can be placed onto the cornea of the eye and used for guiding the gonioscope over its surface. Such a lens 64 is shown in FIG. 7 that illustrates a combination of a gonioscope 20b with a meniscus lens 64. In order to provide some movement of the gonioscope 20b over the lens surface, the small-diameter side of the gonioscope should be smaller than the diameter of the meniscus lens 64. The meniscus lens 64 used in this embodiment should have the curvature on the concave side facing the eye, which matches the curvature of the eye cornea, while on the convex rear side of the lens the curvature may be different. Depending on the ratio of the radii on the concave surfaces, the lens 64 may fulfill different functions such as expanding the field of observation or narrowing the field of observation.

The lens 64 can be glued to the front-end face 66 of the gonioscope 20b with the use of glue 67. In another embodiment, which is shown in FIG. 8, the meniscus lens 64a and the gonioscope 20c are separated from each other.

The lens 64a may have an annular edge 69b for use as a stop that limits angular or swinging movements of the gonioscope relative to the optical axis of the lens 64a that in the position shown in FIG. 7 coincides with the optical axis $O_{1c}$—$O_{1c}$ of the eye. If necessary, the lens can be secured from movements on the eye by a special adapter (not shown) supported by the orbital cavity of the patient's frontal bone.

In this case, the gonioscope 20c can angularly slide over the stationary lens 64a (FIG. 5) and can be installed with respect to the optical axis of the eye 22c at an angle γ that even further broadens the scope of observation of the anterior chamber and the fundus of the eye to the limits of the most hard-to-observe areas.

Figure 8:
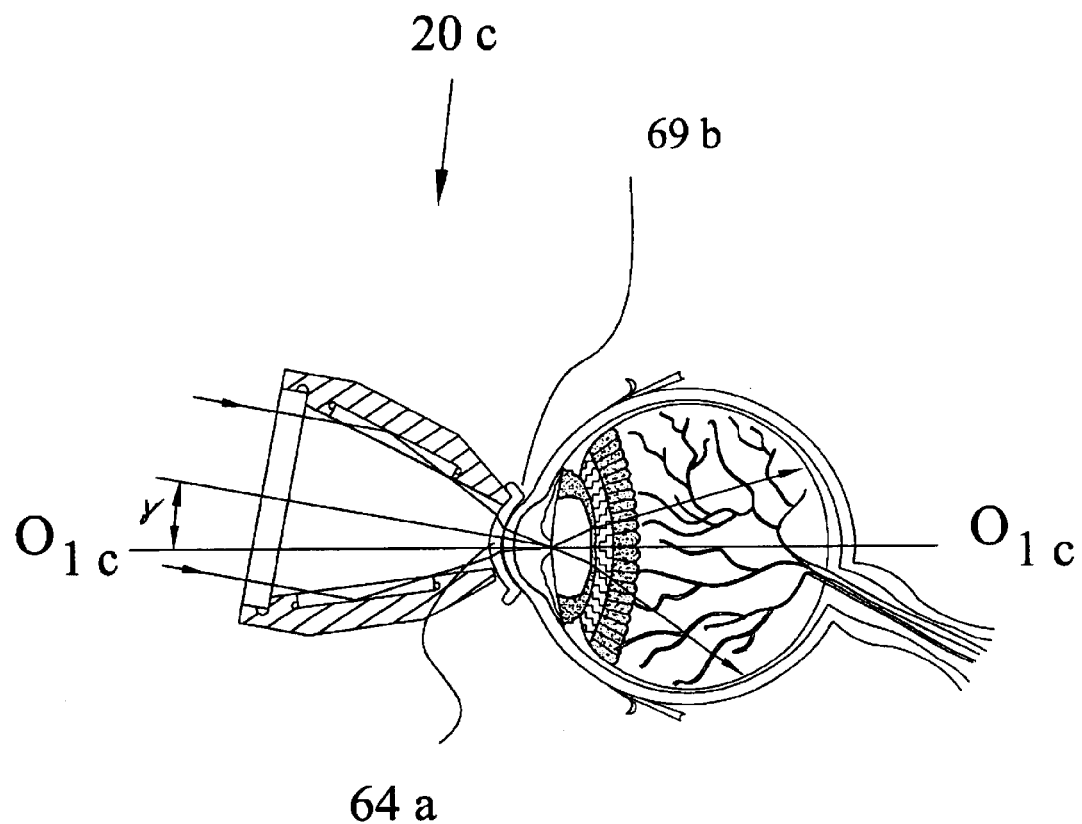
FIG. 8 is a view similar to FIG. 7 illustrating the gonioscope on the meniscus lens in an angular position with respect to the optical axis of the eye.

It is understood that the embodiment shown in FIG. 8 is applicable to a gonioscope of any embodiment described earlier.

Figure 9:
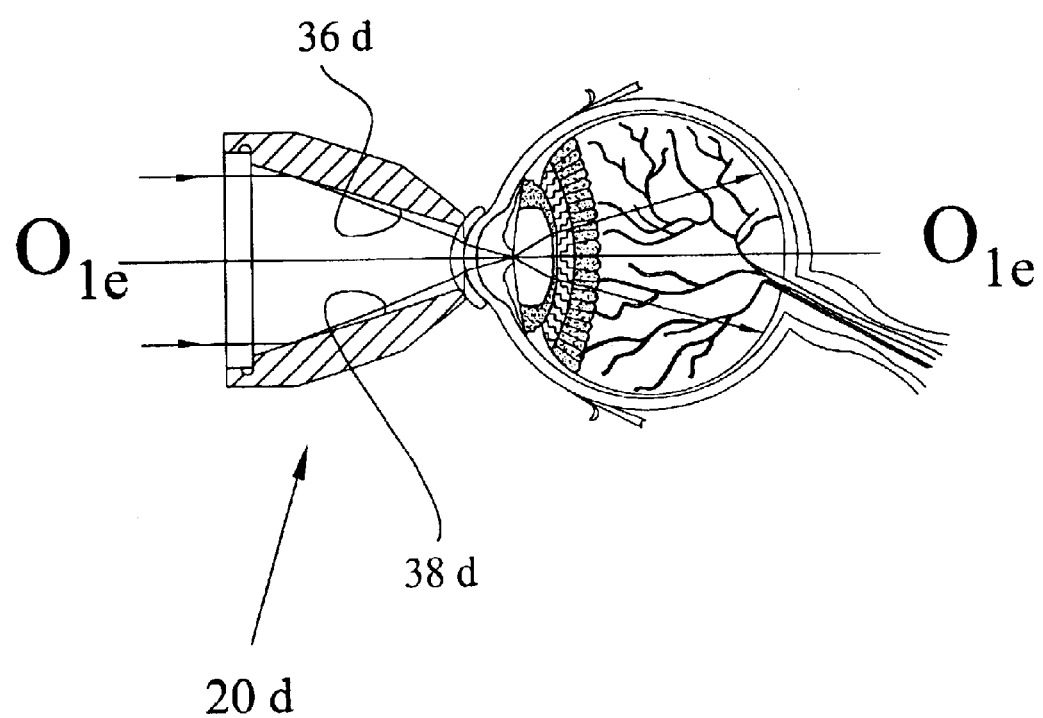
FIG. 9 is a longitudinal sectional view of a monolithic hollow disposable gonioscope of the invention.
Figure 10:
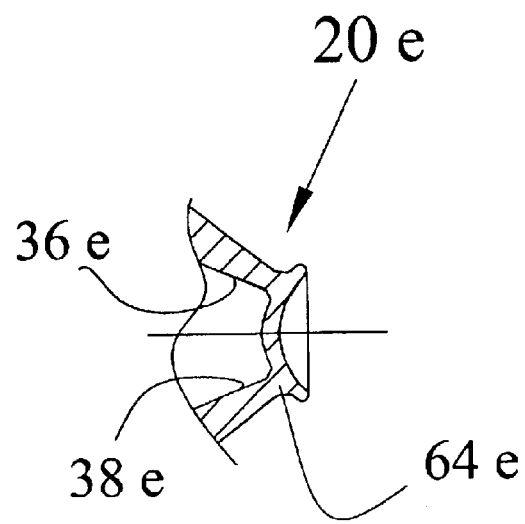
FIG. 10 is a fragmental view of a gonioscope of the invention molded together with the lens shown in FIG. 9.

FIG. 9 is a longitudinal sectional view of a monolithic hollow disposable gonioscope 20d. This device can be formed, e.g., by molding and by forming flat mirror surfaces (only two of which, i.e., 36d and 38d, are shown in FIG. 9) on the inner side of the gonioscope 20d. The rest of the design may be the same as in the previous embodiment. This gonioscope 20e also may be molded together with the lens 64e, as shown in FIG. 10. The mirrors 36d, 38d, . . . (FIG. 9) . . . 36e, 38e, . . . (FIG. 10) are formed by chemical or physical vapor deposition, sputtering, etc., after completion of the molding operation. This gonioscope can be produced from inexpensive moldable plastic with biocompatible properties.

Figure 11:
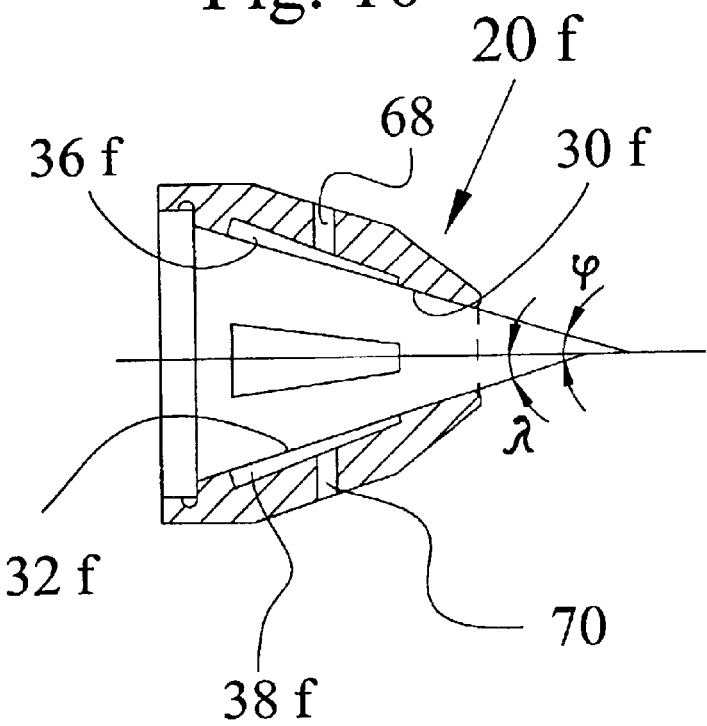
FIG. 11 is a longitudinal sectional view of a gonioscope made in accordance with an embodiment of the invention in which, instead of different angles of inclination on the flats, the different angles of inclination with respect to the longitudinal axis of the gonioscope are formed on the mirror surfaces of the inserts.

FIG. 11 is a longitudinal sectional view of a gonioscope 20f made in accordance with an embodiment of the invention in which, instead of different angles of inclination on the flats 30f and 32f, the different angles φ and λ with respect to the longitudinal axis of the gonioscope are provided on the mirror surfaces of the mirror inserts 36f and 38f. The inserts can be replaceable and have different taper angles φ and λ. For replacement, the inserts 36f and 38f can be secured in their respective recesses by press fit, and the gonioscope body may be provided with openings 68 and 70 for removal of the replaceable inserts by pushing them out from the recesses through the openings.

Thus it has been shown that the present invention provides a gonioscope, which is simple in construction, inexpensive to manufacture, versatile in application, can be produced with different angles of inclination of the flats on the inner surface of the gonioscope, allows observation of the most hard-to-see areas of the fundus, has internal location of mirrors for protection against damage in cleaning and sterilization, can be produced in a disposable form by molding, may be combined with a meniscus lens applied onto the eye cornea, and may have permanent or replaceable mirror inserts with the same or different angles of inclination of the reflecting surfaces with respect to the longitudinal axis of the gonioscope.

The invention has been shown and described with reference to specific embodiments, which should be construed only as examples and do not limit the scope of practical applications of the invention. Therefore any changes and modifications in technological processes, constructions, materials, shapes, and their components are possible, provided these changes do not depart from the scope of the attached patent claims. For example, the material of the gonioscope body may be plastic or metal. Depending on the material, the body can be molded, stamped, or cast. The body can be cast or molded as a single piece with the double-concave lens. The entire inner surface may comprise a continuous mirror conical surface. The cross-section of the inner cavity of the gonioscope may have an oval, elliptical, or rectangular cross-section, i.e., the body may have a truncated conical or pyramidal shape. The gonioscope of the invention may be used in combination with a microscope, a slit lamp, or another optical device. In this case, the cover on the large-diameter side of the gonioscope can be made as an adapter matching the appropriate device. The mirrors are not necessarily flat.

What is claimed is:

1. An optical device for intraocular observation of a patient's eye comprising:
  a hollow tapered body having an outer surface, an inner surface, a small-diameter side which during the use faces the patient's eye, a large-diameter side opposite to said small-diameter side, and a longitudinal axis passing through the centers of said small-diameter side and said large-diameter side;
  at least one mirror located on said inner surface having a mirror surface which is capable of reflecting a light scattered inside the eye and is protected from physical contact; and
  a meniscus lens which is made separately from said small-diameter side, said meniscus lens having an outer edge, a front concave surface, which is intended for placing and securing on the cornea of an eye, and a rear convex surface on the side of said meniscus lens opposite to said front concave surface, wherein said optical device being able of performing angular sliding movement over said convex surface of said meniscus lens and is used as a support for said small-diameter side during said angular sliding movement thereof over said rear convex surface.

2. The optical device according to claim 1, wherein said small-diameter side is smaller than said meniscus lens, an annular projection that extends towards said small-diameter side being formed on said front concave surface that faces said small-diameter side, wherein said annular projections extending towards said small-diameter side from the outer edge of the meniscus lens and wherein said projections effectively limits movement of said small-diameter side with respect to said meniscus lens.

3. An optical device for intraocular observation of a patient's eye comprising:
  a hollow tapered body having an outer surface, an inner surface, a small-diameter side which during the use faces the patient's eye, a large-diameter side opposite to said small-diameter side, and a longitudinal axis passing through the centers of said small-diameter side and said large-diameter side, wherein a plurality of recesses are formed on said inner surface, and inserts made from a transparent material, are inserted into said recesses, and have mirror surfaces formed on the sides of said inserts that face away from said inner surface, said mirror surfaces being arranged at different angles to said longitudinal axis and are capable of reflecting a light scattered inside the eye, said mirror surfaces being protected from physical contact,wherein said inserts having a press fit in said recesses, and hole are made in said hollow tapered body from said outer surface to said recesses for removing said inserts by pushing said inserts out from said recesses through said holes.

4. The optical device according to claim 3, wherein said mirror comprises a coating formed by evaporation in vacuum after forming said hollow tapered body.

* * * * *